United States Patent
Frieze et al.

(10) Patent No.: US 6,244,447 B1
(45) Date of Patent: Jun. 12, 2001

(54) INSTRUMENT BRACKET WITH RESILIENT LOCKING MEANS FOR USE WITH A STERILIZABLE TRAY

(76) Inventors: Marcia A Frieze, 45 Berkery Pl., Alpine, NJ (US) 07620-0472; Allan S. Frieze, 100 Warren St., Jersey City, NJ (US) 07302

( * ) Notice: Subject to any disclaimer, the term of this patent is extended or adjusted under 35 U.S.C. 154(b) by 0 days.

(21) Appl. No.: 09/403,364
(22) PCT Filed: Aug. 28, 1997
(86) PCT No.: PCT/US97/15194
§ 371 Date: Oct. 20, 1999
§ 102(e) Date: Oct. 20, 1999
(87) PCT Pub. No.: WO98/47542
PCT Pub. Date: Oct. 29, 1998

(30) Foreign Application Priority Data

Apr. 22, 1997 (WO) .................................. PCT/US97/06650

(51) Int. Cl.[7] ....................................................... A47F 7/00
(52) U.S. Cl. ...................... 211/85.13; 211/70.6; 211/184; 206/370; 206/438
(58) Field of Search ............................... 211/85.13, 60.1, 211/70.6–70.7, 69, 183–184; 206/370, 438, 443, 363, 561–562, 564–565; 422/26, 297, 300; 220/532–533, 541–542

(56) References Cited

U.S. PATENT DOCUMENTS

| | | | |
|---|---|---|---|
| 3,154,281 | * | 10/1964 | Frank . |
| 3,954,184 | * | 5/1976 | Mendenhall ........................ 211/184 |
| 4,135,868 | * | 1/1979 | Schainholz ........................ 422/300 |
| 4,353,465 | * | 10/1982 | Rado .................................... 206/378 |
| 5,215,726 | * | 6/1993 | Kudla et al. ........................ 422/297 |
| 5,384,103 | * | 1/1995 | Miller ................................. 422/300 |
| 5,433,929 | * | 7/1995 | Riihimaki et al. .................. 422/297 |
| 5,433,930 | * | 7/1995 | Taschner ............................ 422/300 |
| 5,441,709 | * | 8/1995 | Berry, Jr. ............................ 422/297 |
| 5,451,379 | * | 9/1995 | Bowlin, Jr. ......................... 422/297 |
| 5,492,671 | * | 2/1996 | Krafft ................................... 422/26 |
| 5,599,512 | * | 2/1997 | Latulippe et al. .................. 422/300 |
| 5,681,539 | * | 10/1997 | Riley ................................... 422/300 |
| 5,759,502 | * | 6/1998 | Spencer et al. .................... 422/300 |

* cited by examiner

*Primary Examiner*—Daniel P. Stodola
*Assistant Examiner*—Jennifer E. Novosad
(74) *Attorney, Agent, or Firm*—Woodbridge & Associates, P.C.; Richard C. Woodbridge

(57) ABSTRACT

A sterilizable instrument supporting bracket that may be attached to a sterilization tray having spaced perforations. The apparatus includes a resilient body used to support medical instruments. A skeleton structure is located within the resilient body for providing support to the resilient body and includes resilient metal locking devices for attaching the bracket to the tray. The locking devices include two locking numbers having resilient shaft portions that are biased to given position. A head is located to each of the shaft portions with two of the head portions facing in opposite directions. Resilient ribs are attached to the resilient body and are compressed against the tray when the resilient body and related skeleton structure are attached to the tray. The bracket is attached to the tray by squeezing the head portions toward each other and passing them into perforations of the tray and then allowing them to resiliently move outwardly on the shafts to lock the bracket onto the tray. This locking is accomplished by the heads being located within the perforations and the resilient ribs acting to bias the resilient body and skeleton structure away from the tray to maintain engagement.

9 Claims, 6 Drawing Sheets

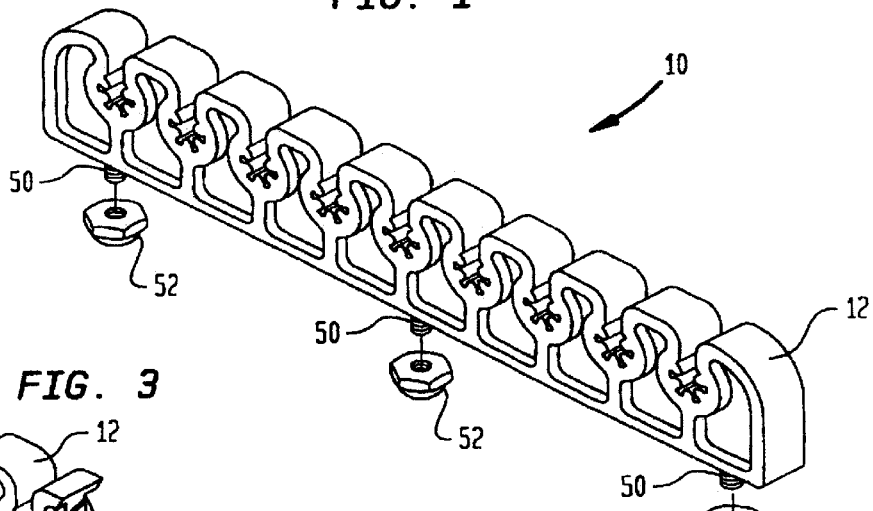
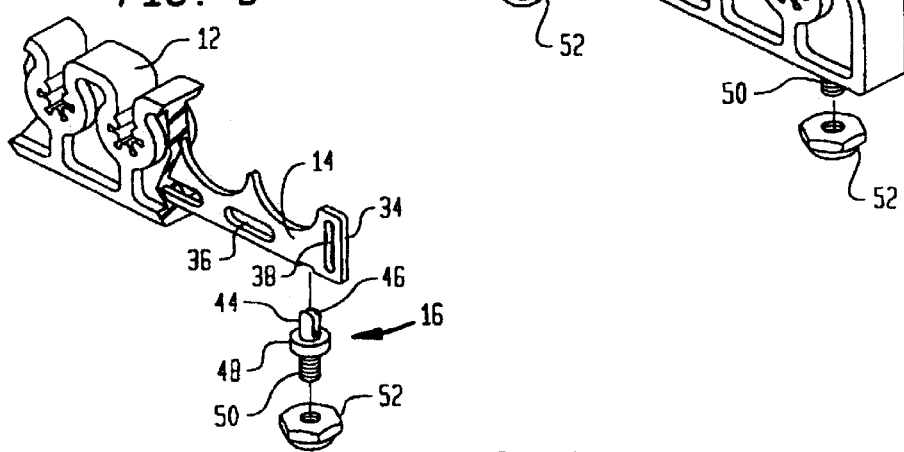
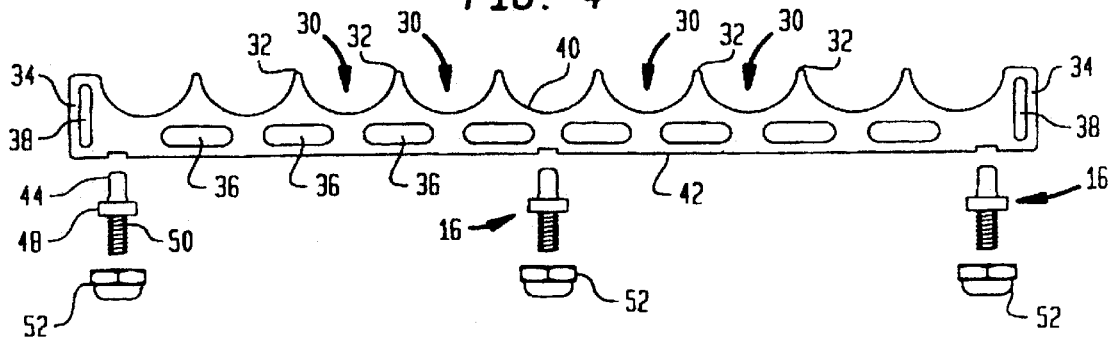
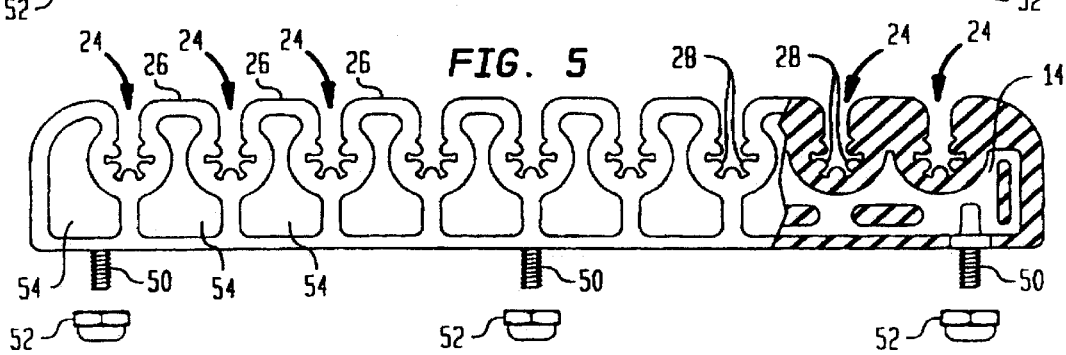

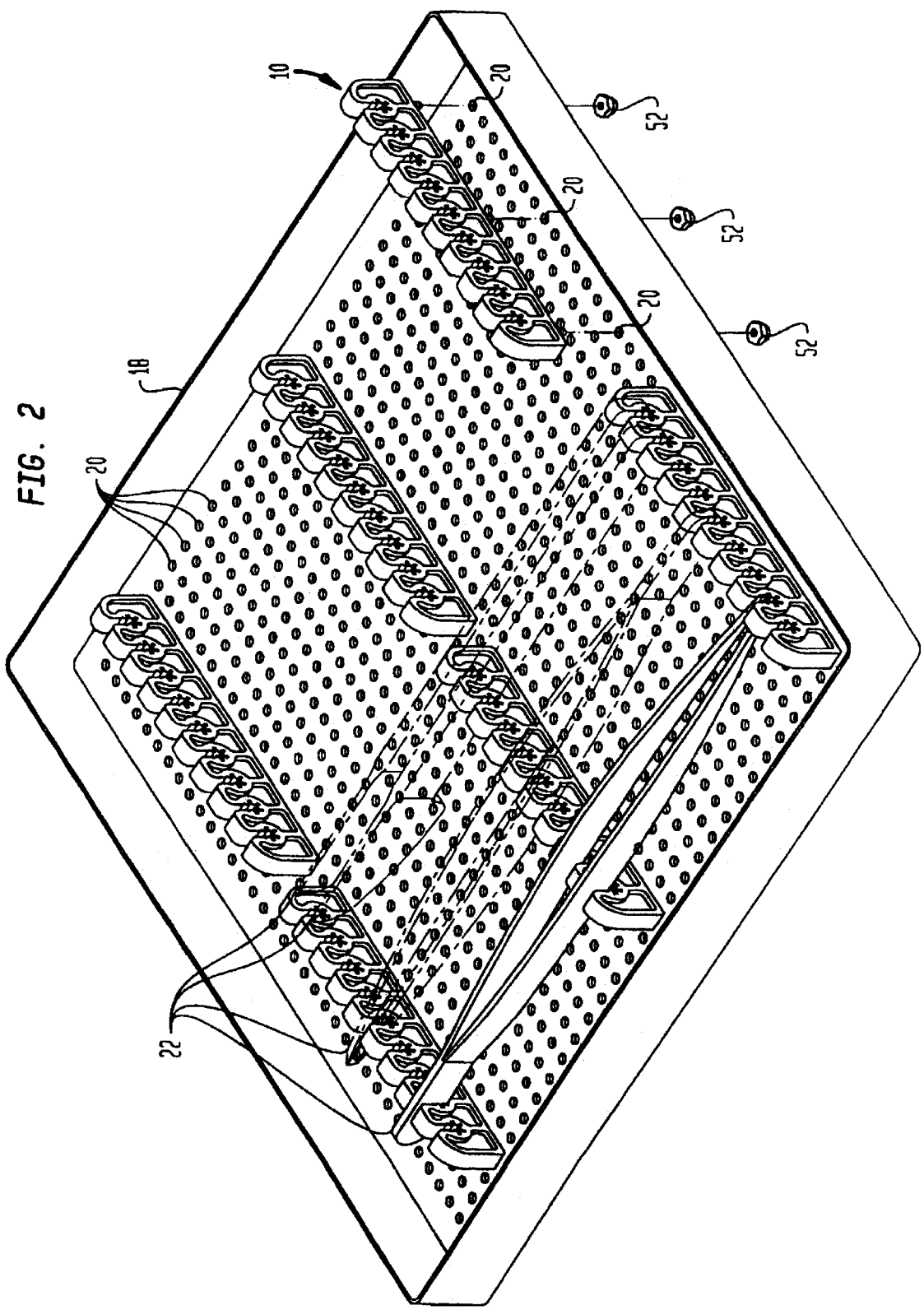

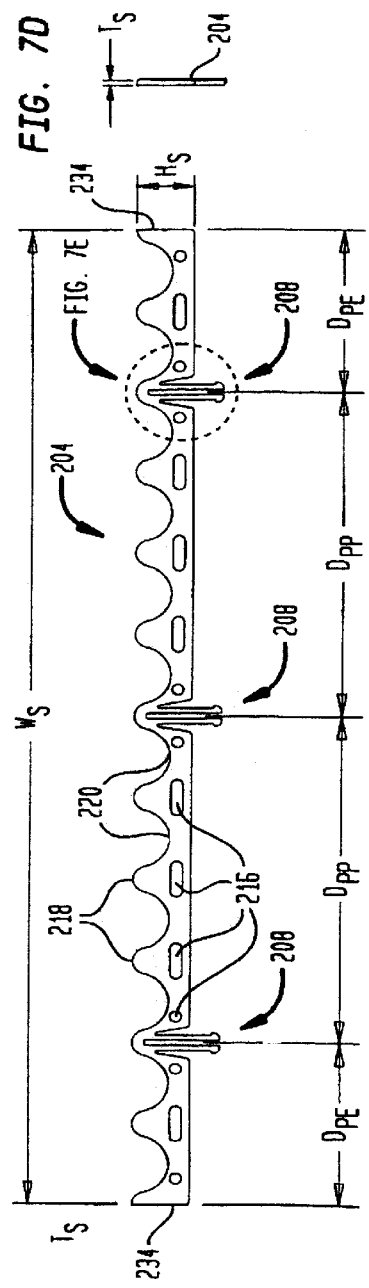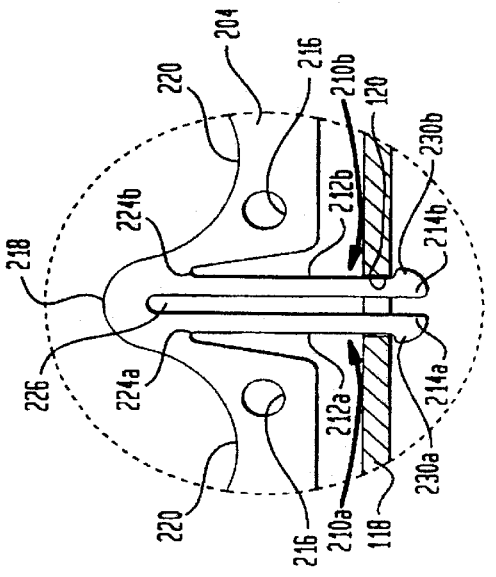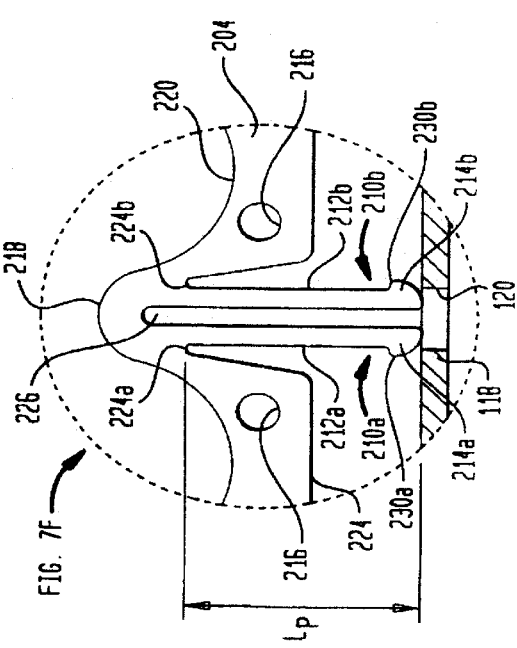

INSTRUMENT BRACKET WITH RESILIENT LOCKING MEANS FOR USE WITH A STERILIZABLE TRAY

CROSS REFERENCE TO RELATED APPLICATIONS

This application is a continuation-in-part of my co-pending international application Ser. No. PCT/US97/06650 having an international filing date of Apr. 22, 1997 and entitled "INSTRUMENT BRACKET FOR USE WITH A STERILIZABLE TRAY", the entire contents of which are hereby incorporated by reference.

BACKGROUND OF THE INVENTION

1. Field of the Invention

The invention comprises a bracket for supporting medical instruments in a sterilizable tray in which the bracket body is formed primarily from resilient silicone and is strengthened by a relatively rigid, spring tempered, metal interior skeleton.

2. Description of Related Art

It is common practice to put medical instruments on trays and place them into high temperature environments for the purposes of sterilization. Steam heated autoclaves are probably the most common device used for killing germs and other biohazards. The instruments to be sterilized are generally placed in trays which, in turn, are placed into the cleansing environment. In order to keep the instruments from moving, it is fairly common practice to separate and support them with brackets.

Instrument supporting brackets can take several different forms. Perhaps the most common form is a custom tray which includes custom made brackets laid out according to the specific request of the customer. An outline of the instrument to be supported is frequently printed on the bottom surface of the tray so that accurate instrument positioning is achieved. It is also common practice to place an English language legend, such as "Russian Tissue Forceps" adjacent to the outline of the desired instrument. The custom made brackets, which generally have an irregular shape, are then permanently attached to the tray with rivets. While such trays have advantages, they have several disadvantages too. First of all, they are expensive and time consuming to produce because each tray has to be individualized for each specific customer's request. Second, brackets are not removable and, therefore, there is no flexibility in the layout of the tray. Instrument holding trays, such as described are sold under the trademark MEDITRAY® by Case Medical, Inc., 65 Railroad Avenue, Ridgefield, N.J. 07657.

Another technique for attaching prior art brackets to a sterilizable tray is to have the brackets slide into a keyway that is provided for on the tray itself.

In an effort to further reduce costs, instrument holding brackets have recently become available which comprise stainless steel or aluminum bodies covered with a thin coat of nylon. The brackets typically have an L-shaped cross section. A pair of studs is attached to the bottom of the L-shaped bracket with nylon serving as the adhesive. The stainless steel or aluminum brackets just described can then be placed selectively or randomly on a tray having a plurality of regularly spaced perforations therein.

While the foregoing describe improvements in the art, they still do not present an optimal structure. What is desired is a bracket that will: withstand high temperatures; provide secure support for heavy instruments, yet light support for delicate instrumentation; provide for complete surrounding by steam; provide for the ability to grab and securely hold heavy and delicate instruments; provide flexibility and strong support at the same time; and, also, provide for the ability to place brackets at a wide variety of locations in order to accommodate a wide spectrum of instruments.

In addition to the foregoing, one of the problems with prior art instrument brackets is the difficulty of efficiently attaching them to a sterilizable tray. One of the most common forms of prior art attachment is to use rivets. Unfortunately, rivet attachments make it impossible to remove a bracket and/or move it around without destroying the tray. Other approaches have been tried, but most tend to be permanent or take a considerable amount of time to attach. The prior art, therefore, appears to be lacking in a simple and efficient mechanism for attaching instrument holders to a sterilizable tray in a secure manner yet, at the same time, permit the instrument holder to be rearranged to accommodate different types of instruments.

It was in the context of the foregoing prior art and the above identified needs that the present invention arose.

SUMMARY OF THE INVENTION

Briefly described, the invention comprises a bracket for supporting medical instruments in a sterilizable tray in which the bracket body is formed primarily from resilient silicone and is strengthened by a relatively rigid metal interior skeleton backbone. The resilient silicone bracket body includes a plurality of medical instrument receiving indentations or valleys separated by intervening peaks. Resilient ribs formed in the instrument receiving indentations gently support the medical instruments and optimally allow sterilizing steam to be exposed to the maximum surface area of the instrument. The spring tempered stainless steel skeleton backbone is encapsulated by the silicone body. The skeleton also includes peaks and valleys that mimic and align with the peaks and valleys of the silicone body and provide additional strength thereto. Flow-through holes or apertures in the skeleton backbone permit the silicone to optimally bond with the backbone. Threaded studs are mechanically attached to the skeleton backbone. Each stud includes a slotted head which attaches to the bottom edge of the stainless steel skeleton backbone, a widened, ring-like midsection, and a threaded end that is distal from the slotted end of the stud. The slotted end and most of the round midsection of the stud are also encapsulated in the silicone. The bracket is preferably attached to the tray by placing the threaded portions of the studs through the perforations in the tray and attaching them thereto with lock nuts.

According to alternative embodiments of the invention, the studs may be replaced by resilient prongs that snap into the vent perforations in the bottom of the tray. Each prong includes a shaft attached at one end to the stainless steel skeleton and includes at the distal end thereof an enlarged head section. According to a first alternative embodiment, the barbs on the head sections of the prongs face away from each other and are separated by a stabilizing foot. Each prong of a pair occupies its own individual perforation hole and is separated by the stabilizing foot which occupies a third hole between the two prongs. According to a second alternative embodiment of the invention, the barbs on the head sections of the prong pairs also face away from each other, but the prongs are located directly adjacent to each other in such a fashion that both prongs snap and lock into the same perforation hole. The two alternative embodiments also include a pair of resilient compressible ribs located on the resilient body of the bracket and on opposite sides of the locking prongs or means. The resilient ribs compress when the prongs are inserted into their respective vent perforation holes and help to provide sufficient pressure on the bracket and the locking prongs to keep the bracket stabile in the locked mode.

The invention may be more fully understood by reference to the following drawings.

BRIEF DESCRIPTION OF THE DRAWINGS

FIG. 1 is a perspective view of the preferred embodiment of the sterilizable instrument bracket.

FIG. 2 is a perspective view of the preferred embodiment of the invention illustrated in FIG. 1 shown in the process of being placed into a sterilizable tray and locked with respect thereto with lock nuts.

FIG. 3 is a partial, perspective cross sectional view of the bracket illustrated in FIG. 1 showing the manner in which the slotted head of the studs are attached to the relatively rigid spring tempered skeleton backbone.

FIG. 4 is a front, exploded view illustrating the manner in which the attachment studs are connected to the skeleton backbone.

FIG. 5 is a partial, front cross sectional view of the fully assembled bracket.

FIG. 7C is a front elevational view of the stainless steel skeleton found inside of the second alternative embodiment of the invention illustrated in FIG. 7A.

FIG. 7D is a side elevational view of the stainless steel skeleton shown in FIG. 7C.

FIG. 7E illustrates the stainless steel skeleton of FIG. 7C prior to inserting the prong pair of locking means into the vent perforations in the base of a sterilizable tray.

FIG. 7F illustrates the prong pair of the locking means shown in FIG. 7E after they have passed through the same vent perforation in the base of a sterilizable tray.

DETAILED DESCRIPTION OF THE INVENTION

Figure 6A:
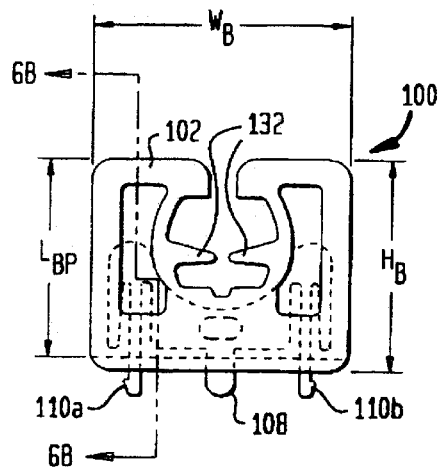
FIG. 6A is a front elevational view of a first alternative embodiment of the invention, intended to support only one medical instrument, and employing resilient locking means and further showing a pair of prongs, each having barbs on their head sections facing in opposite directions, separated by a stabilizing foot.

During the course of this description like numbers will be used to identify like elements according to the different views that illustrate the invention.

The preferred embodiment of the invention 10 is illustrated in a perspective view in FIG. 1. The three major structural components of the preferred embodiment 10 are a resilient silicone body 12, a skeleton backbone 14 encapsulated by the silicone body 12 and a plurality of threaded studs 16 partially encapsulated by the silicone body 12.

Bracket 10 is preferably attached to a sterilizable tray 18 such as illustrated in FIG. 2. Tray 18 includes a plurality of regularly spaced perforations or apertures 20 for receiving the threaded sections 50 of studs 16 of bracket 10. The threaded section or end 50 of studs 16 pass through the perforations 20 and are locked with respect thereto by lock nuts 52 which threadably attach to the threaded portion 50 on the portion of stud 16 opposite from the silicone body 12. Alternate methods could also be employed to attach studs 16 to tray 18. For example, the threaded sections 50 of the studs 16 could be smooth or threaded and a push on clip could be used instead of lock nuts 52 to secure the bracket 10 to the apertures 20 in tray 18. A plurality of different medical instruments 22 are supported by brackets 10 as shown in FIG. 2. Threaded studs 16 are located at intervals identical to the spacing between perforations 20 in tray 18 so that the brackets 10 may be placed in any arrangement for supporting medical instruments 22. Therefore, it is easy to rearrange the brackets to accommodate a wide variety of different medical instruments 22 which may vary substantially in size, weight and shape.

Details of the silicone body 12, its related relatively rigid spring tempered skeleton backbone 14, and threaded support studs 16 will be more fully appreciated by referring to FIGS. 3–5.

Medical instruments 22 are received in indentations or valleys 24 in the resilient silicone body 12. The medical receiving indentations are separated by resilient peaks 26. Ribs 28 located at regular intervals inside of the instrument receiving indentations 24 provide gentle yet firm support for the medical instruments 22. More importantly, ribs 28 permit sterilizing steam to circulate in between so as to further assist in the killing of biohazardous germs and materials. There is a small gap between adjacent peaks 26 and the valleys 24 so as to further hold and secure an instrument 22 in the bracket 10.

The profile of the relatively rigid spring tempered stainless steel skeleton backbone 14 generally mimics the profile of the peaks 26 and valleys 24 of the resilient silicone body 12. Skeleton backbone 14, therefore, includes valleys 30 separated by peaks 32. Each skeleton backbone 14 also includes a top edge 40, which incorporates peaks 32, and valleys 30, a bottom edge 42 which is attached to studs 16, and a pair of side ends 34. Flow through apertures 36 are located along the length of skeleton backbone 14. Likewise a pair of flow through holes or apertures 38, oriented perpendicularly to flow through apertures 36, are located in the side ends 34 of skeleton backbone 14.

Each stud 16 includes a head 44, a ring shaped midsection 48 in the middle thereof, and a threaded end or section 50 distal from head 44. A skeleton receiving slot 46 is located in stud head 44. The slot 46 in stud head 44 is slightly smaller than the width of the skeleton backbone 14 so that it mechanically locks onto the bottom edge 42 of the skeleton backbone 14. For additional security it may be desirable to weld the slotted head 44 to the bottom edge 42 of the skeleton backbone 14. The ring shaped midsection 44 of stud 16 supports the bottom edge 42 of the skeleton backbone 14.

The bracket 10, according to its preferred embodiment, is constructed in the following manner. First, the bottom edge 42 of the backbone 14 is placed into the slot 46 in the head 44 of stud 16. Three studs 16 are shown in FIGS. 1–5 but two studs 16 or four or more studs 16 could also be used according to the demands of the use. Studs 16 are preferably placed at regular intervals identical to the spacing between perforations 20 in tray 18 as previously described. Stud heads 44 are then mechanically attached to the bottom edge 42 of skeleton backbone 14 either by crimping or by welding, or both. Second, the skeleton backbone 14 with studs 16 attached is then placed into a mold in which silicone is injected to form resilient body 12. The silicone completely encapsulates the skeleton backbone 14. Flow through apertures 36 and 38 in skeleton backbone 14 further assist in mechanically anchoring the silicone body 12 to the skeleton backbone 14. As previously described, the silicone also encapsulates the head 44 and most of the midsection 48 of stud 16. The exposed portion of the midsection 48 of stud 16 also serves as a stop for the bracket 10 when it is placed in position on tray 18. The resulting molded silicone bracket 10 includes sculpted indents 54 in the sides of the silicone bracket body 12. Sculpted indents 54 help to conserve weight and space.

The invention described thus far has several significant, nonobvious advantages over the prior art. First, it provides for substantial versatility for permanent or semi-permanent fixturing of brackets 10 with respect to instruments. Second, it provides important structural support for heavy instruments 22, yet protects delicate instruments 22. Third, the encapsulated metal 14 cannot damage delicate instrumentation 22. Fourth, the flexible silicone ribs 28 provide grip with minimal contact of the instrument 22 to the bracket surface, yet permits optimum sterilization. Presently existing prior art brackets do not allow for optimal sterilization, as they tend to be bulky and grip a large surface area of the instrument 22. Fifth, the spring tempered metal skeleton 14 permits the bracket 10 to adjust slightly so that the threaded portion 50 of the studs 16 can align with perforations 20 in the tray 18 even if there isn't perfect spacing.

A first alternative embodiment 100 of the invention is illustrated in FIGS. 6A–6H. Embodiment 100 includes a silicone body 102 and a stainless steel skeleton or backbone 104 both similar to, but not identical to, the preferred embodiment 10. The bottom portion of the silicone body 102 includes a pair of parallel, compressible ribs 106a and 106b shown in detail in FIGS. 6C and 6D. Compressible ribs 106a and 106b lie on opposite sides of a stabilizing tab or control foot 108 seen in FIG. 6A. Stabilizing foot 108 is located between a pair of opposite facing resilient locking prongs 110a and 110b.

Figure 6B:
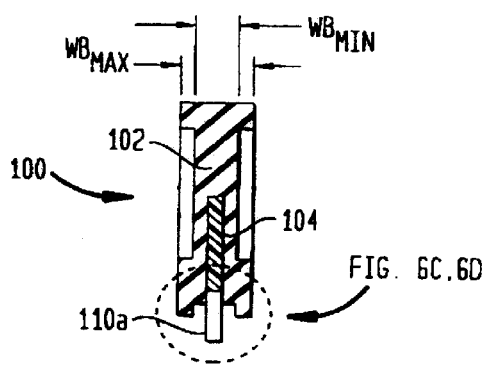
FIG. 6B is a cross-sectional view of the first alternative embodiment of the invention illustrated in FIG. 6A.
Figure 6C:
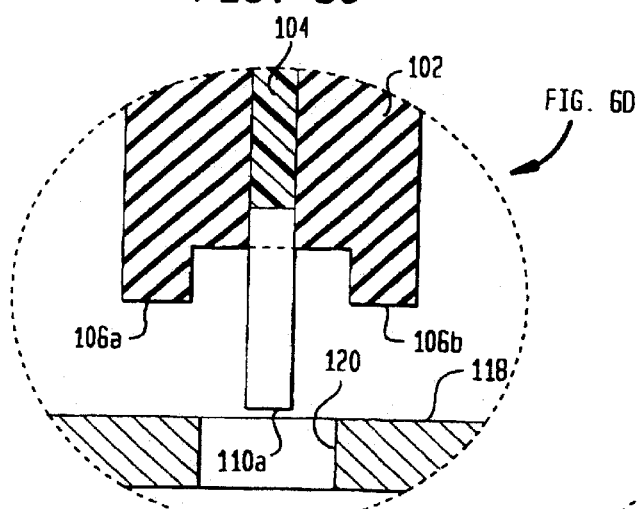
FIG. 6C is a detail, cross-sectional view of the lower portion of the bracket illustrated in FIG. 6B showing the compressible ribs prior to compression.
Figure 6D:
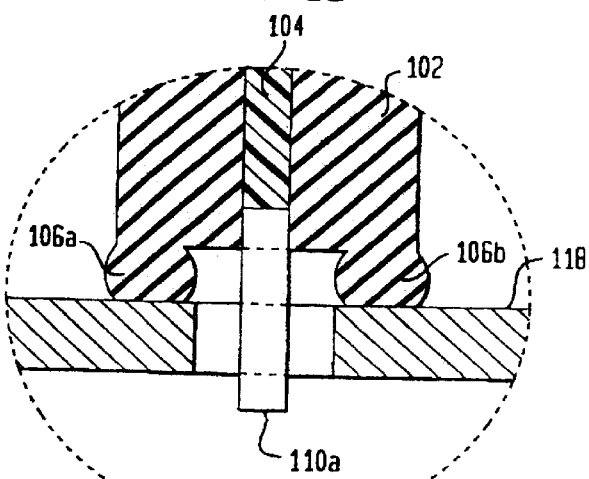
FIG. 6D is another detail view of the lower portion of the first alternative embodiment of the invention illustrated in FIG. 6B showing the compressible ribs under compression after the locking means have locked into position in the vent perforations of a sterilizable tray.
Figure 6F:
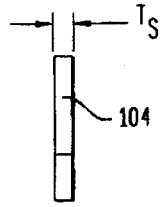
FIG. 6F is a side elevational view of the stainless steel skeleton illustrated in FIG. 6E.
Figure 6E:
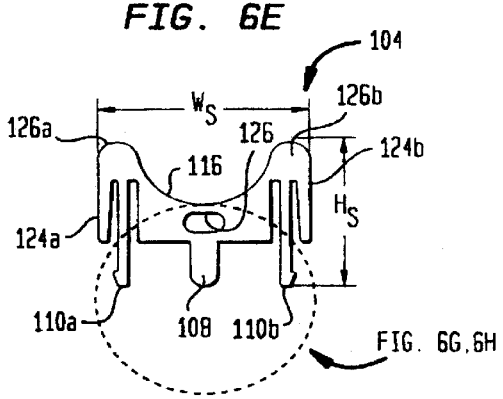
FIG. 6E is a front elevational view of the stainless steel skeleton, or backbone, employed with the first alternative embodiment of the invention illustrated in FIG. 6A.
Figure 6G:
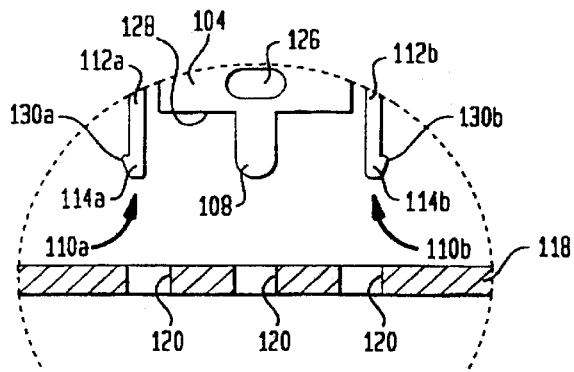
FIG. 6G illustrates a detail of the stainless steel skeleton illustrated in FIG. 6E prior to the resilient locking means engaging the vent perforations in the base of a sterilizable tray.
Figure 6H:
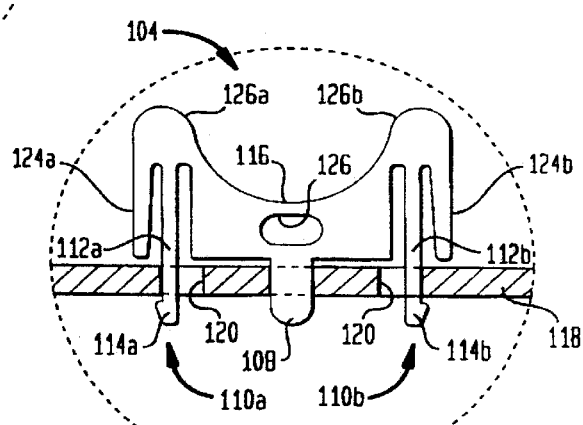
FIG. 6H illustrates the stainless steel skeleton shown in FIG. 6G after the locking means have engaged the vent perforations in the base of a sterilizable tray.

Details of the resilient locking prongs 110a and 110b may be more easily understood by reference to FIGS. 6E, 6G and 6H. The resilient locking prongs 110a and 110b in combination with a stabilizer foot 108 comprise a resilient locking means which holds the first alternative embodiment of the bracket 100 in position with respect to the base 118 of the sterilizable tray. Each of the resilient prongs 110a and 110b include a shaft portion 112a and 112b attached at one end to the stainless steel backbone 104 and at the distal end thereof a bead 114a and 114b. Each of the heads 114a and 114b, respectively, include a barb portion 130a and 130b which face in opposite directions from each other. The stainless steel skeleton 104 includes a saddle portion 116 located half way between upper tips 126a and 126b. A pair of downward directed, wing-like projections 124a and 124b are located on opposite sides of the stainless steel skeleton 104. A flow through hole 126 permits the silicone material of the silicone body 102 to pass through the stainless steel skeleton 104 and reinforces its strength. Stainless steel skeleton 104 also includes a lower edge 128 that defines the bottom portion of the main body of the element. The first alternative embodiment 100 described in FIGS. 6A–6H is especially suited for use with a single medical instrument. The same technique could, however, be used for a larger bracket if desired.

The first alternative embodiment 100 is connected to the base 118 of a tray in the following manner. First, the resilient prongs 110a and 110b are squeezed towards each other so that they can pass through vent holes 120 in the base 118 of the tray (see FIGS. 6C and 6G). Second, the resilient prongs 110a and 110b are inserted into the holes 120 which causes the compressible silicone ribs 106a and 106b to begin to compress. Third, and last, the oppositely facing barbs 130a and 130b spring outwardly after they pass sufficiently far through the vent holes 120 so that the resilient prongs 110a and 110b lock into position. In the meantime, the stabilizing foot 108 also passes through an intermediate aperture 120 and fits snugly therein. Simultaneously, the compressible ribs 106a and 106b are at maximum compression as seen in FIGS. 6D. The ridges or ribs 106a and 106b compress to account for use with different materials or different thicknesses of the tray base 118. According to the preferred embodiment of the invention, the first alternative embodiment 100 has a height of $H_B$ of 1.070 inches, a width $W_B$ of 1.150 inches and a length measured from the top of the bracket 100 to the bottom portion of the silicone body adjacent to foot 108 of $L_{BP}$ of 1.00 inches as seen in FIG. 6A. As shown in FIG. 6B, the first alternative embodiment 100 has a maximum width of $W_B$ max=0.350 inches and a minimum width $W_B$ min of 0.225 inches. Similarly, the stainless steel skeleton 104 has a preferred width of $W_S$ of 0.05 inches, and a height of $H_S$ of 0.73 inches, as shown in FIG. 6E, and a width $T_S$ of 0.05 inches, as shown in FIG. 6F.

One of the major advantages of the first alternative embodiment 100 is that the resilient prongs 110a and 110b can snap into plastic trays 0.125 inches thick and metal trays as thin as 0.05 inches thick or any combination of materials from 0.040 inches to 0.150 inches thick. The single prong per hole structure of the first alternative embodiment 100 requires a stabilizing foot or tab 108 so that the locking prongs 110a and 110b will not bend beyond their yield strength. The stainless steel spine 104 is preferably formed from spring tempered stainless steel such as ¾ inch hard no. 301 or no. 400 spring tempered stainless steel. The silicone body 102 is preferably a material having a durometer in the range of 30–50. The foot or tab 108 has two purposes. The first is to assist in the location of the holes 120 in the tray bottom 118 and the second is to prevent the overstressing of the resilient prongs 110a and 110b. In addition, the two compressible ribs 106a and 106b located on opposite sides of the stabilizer foot 108 provide spring tensioning to make up for the varying thicknesses of the tray base or bottom 118.

In order to remove the bracket 104, a pair of pliers can be employed, or a special tool can be used, which squeeze the barbs 130a and 130b inwardly, towards each other, so that the bracket 100 can be grasped and the prongs 110a and 110b pulled out of their respective apertures 120. In this manner the bracket 100 can be reused or relocated.

A second alternative embodiment 200 employing resilient prong pairs 208 is illustrated in FIGS. 7A–7F. Second alternative embodiment 200 includes a silicone body 202 attached to a stainless steel skeleton 204. A pair of resilient, compressible ribs 206a and 206b are located at the bottom of the silicone body 202 and on opposite sides of the resilient locking means 208. Details of the skeleton or spine 204 can be more fully understood by reference to FIGS. 7C–7F. As seen in greater detail in FIG. 7E, the resilient locking means 208 comprises a pair of resilient prongs 210a and 210b. Resilient prong 210a includes a shaft 212a and a head portion 214a. Head portion 214a includes a barb 230a shown facing to the left. Similarly, resilient prong 210b includes a shaft portion 212b attached to the skeleton 204 and a head portion 214b attached to the opposite or distal end of shaft 212b. Head portion 214b includes a right facing barb 230b which faces in the opposite direction from barb 230a previously described. Resilient prongs 210a and 210b are fairly long and extend a distance $L_P$ from the base or bottom 224 of the skeleton 204 into the interior of the skeleton 204 as seen in detail in FIGS. 7E and 7F. In other words, the length of prongs 210 and 210b considerably exceeds the distance from skeleton base 224 to the tip of the head portions 214a and 214b.

Each skeleton 204 preferably includes a plurality of circular, or oblong, flow-through holes 216 whose purpose is similar to that previously described with reference to flow-through holes 126 of the first alternative embodiment 100. The bottom edge 224 of the stainless steel skeleton 204 is relatively flat except for the location of the dual locking means 208. In contrast, the upper surface of skeleton 204 comprises a series of peaks 218 and valleys 220. Peaks 218 permit the shafts 212a and 212b of prongs 210a and 210b, respectively, to extend significantly into the body of the stainless steel skeleton 204 thereby providing substantially more resilience for the prongs 210a and 210b. The foregoing structure creates a pair of small valleys 224a and 224b on the outsides of prongs 210a and 210b and a longer valley 226 between prongs 210a and 210b.

The second alternative embodiment 200 is attached to the base 118 of a sterilizable tray in the following manner. First, the resilient locking means 208, comprising a pair of prongs 210a and 210b as shown in FIG. 7E is positioned over the vent perforations 120 of the sterilizable tray 118. Second, pressure is applied to the top of the second alternative embodiment 200 to insert the prongs 210a and 210b into vent aperture 120. Because of the slanted face of the head portions 214a and 214b of barbs 230a and 230b, the aperture 120 naturally cams or squeezes the prongs 210a and 210b so that they fit into aperture 120. Third, continual pressure applied on the top of the second alternative embodiment bracket 200 causes the head portions 214a and 214b to pass through aperture 120 and snap into the locked position as shown in FIG. 7F. In this position the barbs 230a and 230b resiliently move to a position beyond the outside periphery of the aperture 120 and are resistant to removal. When the prongs 210a and 210b are in the position shown in FIG. 7F, the second alternative embodiment 200 is firmly attached to the tray base 118 and cannot be removed of dislodged easily.

In order to remove the second alternative embodiment bracket 200, it is merely necessary to pinch or squeeze the two head portions 214a and 214b of each of the pairs 208 together and, at the same time, gently pull on the bracket 200 on the opposite side thereby permitting the barbs 230a and 230b to pass back through vent perforations 120 and release when they emerge on the opposite side of the apertures 120. Prongs 210a and 210b may be squeezed together either manually or with the assistance of needle nose pliers or similar instruments. In this manner, the bracket 200 may be either removed or rearranged in a more suitable manner depending upon the type of instruments to be sterilized with the tray 118.

Figure 7A:
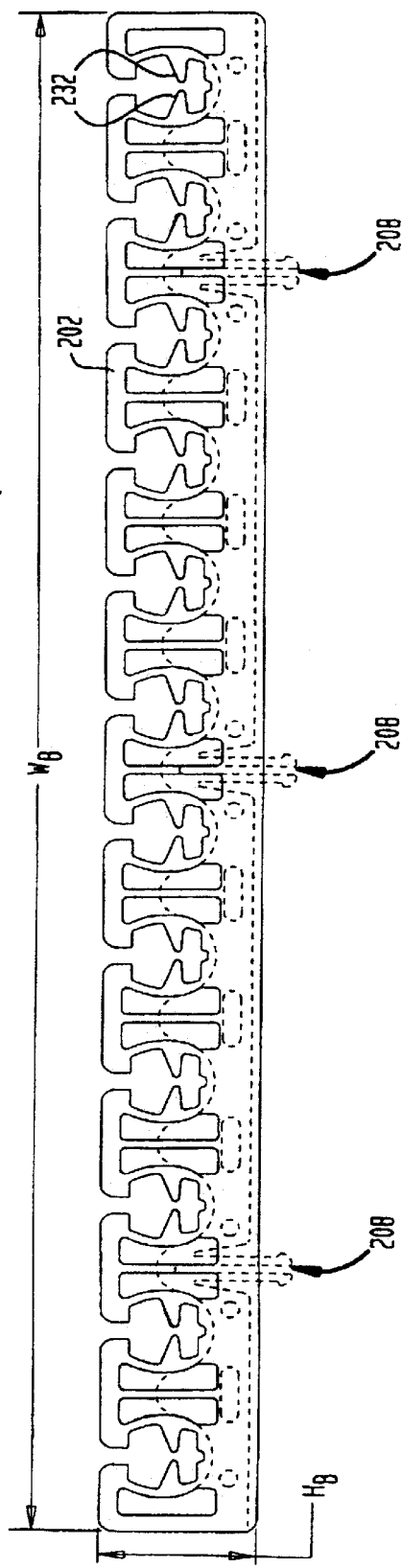
FIG. 7A is a front elevational view of a second alternative embodiment of the invention, intended to support multiple medical instruments, in which the resilient locking means comprises a pair of prongs located adjacent to each other so that they can both be inserted into the same vent hole in the bottom of a sterilizable tray.
Figure 7B:
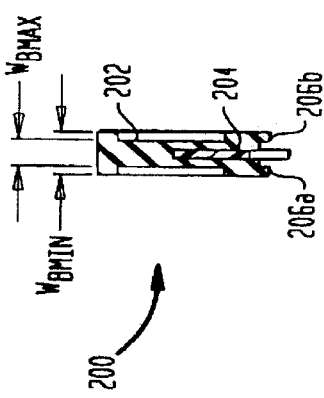
FIG. 7B is a cross-sectional view of the second alternative embodiment of the invention shown in FIG. 7A.

The dual locking tab or prong embodiment 200 is especially useful for long brackets such as illustrated in FIG. 7A. The bracket 200 shown in FIG. 7A has a preferred width $W_B$ of 9.4 inches and a height $H_B$ of 1.07 inches. As seen in FIG. 7B, the maximum width $W_{B\ max}$ of the bracket 200 is 0.35 inches and the minimum width as measured to the interior of the silicone body 204 is $W_{B\ min}$=0.225 inches. The stainless steel skeleton 204, as shown in FIG. 7C, has a preferred width $W_S$ of 9.087 inches and a height $H_S$ of 0.482 inches. The distance from each end 234 of the spine 204 to the first pair of resilient locking means 208 is $D_{PE}$ approximately 1.544 inches, and the distance between resilient locking pairs 208 $D_{PP}$ is approximately 3.000 inches. Lastly, as shown in FIG. 7D, the preferred thickness $T_S$ of skeleton 204 is approximately 0.05 inches. The materials employed with respect to the dual locking tab, second alternative embodiment 200 are essentially the same as the materials employed with the single locking tab first embodiment 100, previously described. The first alternative embodiment 100 includes flexible silicone fingers 132 for the purpose of grabbing a single instrument and, similarly, the second alternative embodiment 200 includes flexible silicone fingers 232 also. The silicone fingers 132 and 232 are appropriate for grabbing 10 mm instruments above fingers 132 and 232 and for containing 5 mm instruments below fingers 132 and 232. As previously described single locking tab, first alternative embodiment 100 including the stabilizing foot 108, is especially appropriate for small brackets. In contrast, the dual locking tab, second alternative embodiment 200, where both resilient prongs 210a and 210b pass through the same aperture 120, is especially appropriate for larger brackets.

While the invention has been described with reference to the preferred embodiment thereof, it will be appreciate by those of ordinary skill in the art that modifications can be made to the structure and form of the invention without departing from the spirit and scope thereof.

We claim:

1. A sterilizable instrument supporting bracket apparatus (100, 200) for attachment to a tray (118) having regularly spaced vent perforations (120) therein, said apparatus comprising:

a resilient body (102, 202);

instrument supporting means (132, 232) located on said resilient body (102, 202) for supporting at least one medical instrument;

skeleton means (104, 204) located within said resilient body (102, 202) for providing support to said resilient body (102, 202);

resilient metal locking means (110a, 110b, 210a, 210b) attached to said skeleton means (104, 204) for attaching said bracket apparatus (100, 200) to said tray (118), said resilient metal locking means (110a, 110b, 210a, 210b) comprising at least a first locking means (110a, 210*a*) and a second locking means (110*b*, 210*b*) attached to said skeleton means (104, 204) and in which said locking means (110*a*, 110*b*, 210*a*, 210*b*) biased to a given position and each include a resilient shaft portion (112*a*, 112*b*, 212*a*, 212*b*) are biased to a given position and attached to said skeleton means (104, 204) and a head portion (114*a*, 114*b*, 214*a*, 214*b*) attached to said shaft portion (112*a*, 112*b*, 212*a*, 212*b*) and wherein at least two of said head portions (114*a* & 214*a*, 114*b* & 214*b*) face in opposite directions; and, resilient ribs (106*a*, 106*b*, 206*a*, 206*b*) attached to said resilient body (102, 202) that may be compressed against said tray (118) when said first and second locking means (110*a*, 110*b*, 210*a*, 210*b*) are passed into said perforations (120), wherein said bracket apparatus (100, 200) is attachable to said tray (118) by squeezing said head portions (114*a*, 114*b*, 214*a*, 214*b*) toward each other and passing them into said vent perforations (120) so that they afterwards expand away from each other and lock into said perforations (120) as the resilient shaft portions (112*a*, 112*b* 212*a*, 212*b*) return to their given positions.

2. The apparatus of claim 1 wherein said first (110*a*) and said second (110*b*) locking means are located to each respectively engage different perforations (120) in said tray (118).

3. The apparatus of claim 2 further comprising:

a stabilizing foot means (108) for engaging a perforation (120) located between the perforations (120) engaged by said first (110*a*) and second (110*b*) locking means.

4. The apparatus of claim 1 wherein said first (210*a*) and second (210*b*) locking means (208) are located adjacent each other and are adapted to pass through the same perforation (120) when said locking means (208) engage said tray (118).

5. The apparatus of claim 1 wherein said shaft (112*a*, 112*b*, 212*a*, 212*b*) has a length ($L_p$), said skeleton (104, 204) has a bottom (128, 222) that is configured to make contact with said tray (118), said bottom (128, 222) being generally perpendicular to said length ($L_p$) of said shaft (112*a*, 112*b*, 212*a*, 212*b*) and located at a position along said length ($L_p$), and said length ($L_p$) being longer than the maximum distance from said bottom (128, 222) of said skeleton (104, 204) to the head portion (112*a*, 112*b*, 212*a*, 212*b*) of said locking means (110*a*, 110*b*, 210*a*, 210*b*).

6. The apparatus of claim 1 wherein said resilient metal locking means (110*a*, 110*b*, 210*a*, 210*b*) is made of spring tempered stainless steel.

7. The apparatus of claim 6 wherein said resilient body (102, 202) is made of silicone.

8. The apparatus of claim 7 wherein said skeleton means (104, 204) is made of spring tempered stainless steel.

9. The apparatus of claim 8 wherein said resilient metal locking means (110*a*, 110*b*, 210*a*, 210*b*) and said skeleton means (104, 204) are fixedly attached to form a unitary member.

\* \* \* \* \*